United States Patent [19]

Ury et al.

[11] Patent Number: 5,247,178
[45] Date of Patent: Sep. 21, 1993

[54] METHOD AND APPARATUS FOR TREATING FLUIDS BY FOCUSING REFLECTED LIGHT ON A THIN FLUID LAYER

[75] Inventors: Michael G. Ury, Bethesda; John T. Phillips, Gaithersburg, both of Md.

[73] Assignee: Fusion Systems Corporation, Rockville, Md.

[21] Appl. No.: 805,498

[22] Filed: Dec. 12, 1991

[51] Int. Cl.⁵ .................................................. A61L 2/10
[52] U.S. Cl. ................................ 250/438; 250/432 R; 250/455.11; 422/24; 210/748
[58] Field of Search .............. 250/435, 438, 432 R, 250/455.1, 436; 422/24; 210/748

[56] References Cited

U.S. PATENT DOCUMENTS

| | | | |
|---|---|---|---|
| 1,145,140 | 7/1915 | Helbronner et al. | 422/24 |
| 2,578,414 | 12/1951 | Foulds | 250/438 |
| 4,694,179 | 9/1987 | Lew et al. | 250/431 |
| 4,766,321 | 8/1988 | Lew et al. | 250/431 |
| 4,798,702 | 1/1989 | Tucker | 422/24 |
| 4,909,931 | 3/1990 | Bibi | 250/438 |
| 4,948,980 | 8/1990 | Wedekamp | 250/504 R |
| 4,968,891 | 11/1990 | Jhawar et al. | 250/438 |
| 5,114,684 | 5/1992 | Walker | 422/186 |

FOREIGN PATENT DOCUMENTS

| | | | |
|---|---|---|---|
| 2736160 | 2/1979 | Fed. Rep. of Germany | 250/435 |
| 90/06899 | 6/1990 | World Int. Prop. O. | 422/24 |

*Primary Examiner*—Jack I. Berman
*Assistant Examiner*—James Beyer
*Attorney, Agent, or Firm*—Pollock, Vande Sande & Priddy

[57] ABSTRACT

Apparatus for treating a fluid by irradiating a thin film of the fluid with high intensity, concentrated light. The irradiation affects chemical physical or biological activity changes in the fluid.

5 Claims, 5 Drawing Sheets

METHOD AND APPARATUS FOR TREATING FLUIDS BY FOCUSING REFLECTED LIGHT ON A THIN FLUID LAYER

The present invention relates to a method and apparatus for treating fluids with radiant energy.

BACKGROUND OF THE INVENTION

It is often necessary to treat a fluid with optical spectral energy which may be infrared, ultraviolet or visible light. The irradiation may be used to cause chemical, physical or biological changes, such as by inducing the reaction of two constituent chemicals, by heating or by sterilizing, respectively. The absorption of light by the fluid attenuates the light so that fluid beneath the surface is irradiated with light which is less intense than the light at the fluid surface.

U.S. Pat. No. 4,831,268 to Fisch et al., U.S. Pat. No. 4,327,276 to Injushin et al., U.S. Pat. No. 1,091,221 to Henri et al. and U.S. Pat. No. 1,038,631 to Neveu all disclose methods or apparatus for treating a fluid by irradiation. None of these references disclose a method or apparatus in which the fluid is constrained to flow in a layer which is thin with respect to the direction of the irradiating rays, and thus a portion of the fluid which flows or is stagnant further from the source of light receives only that light which has been attenuated by the fluid closer to the source. The gradient of light intensity depends on the power of the source, and results in either only the surface of the fluid being treated, or an unnecessarily high intensity of light at the surface which results in an inefficient utilization of light or an adverse affect on the fluid, such as its decomposition.

U.S. Pat. No. 2,065,054 to Creighton et al., U.S. Pat. No. 1,307,500 to Keyes et al. and, U.S. Pat. No. 1,145,140 to Henri et al. all disclose apparatus for treating fluids with light in which the fluid is presented as a thin film to the irradiating light. These references disclose apparatus for radiating the light from a source in an isotropic, non-focused way. Such light which is not focused typically is not intense enough to penetrate fluids which absorb light, unless impractically high power is used.

SUMMARY OF THE INVENTION

Accordingly, it is an object of this invention to provide a method and apparatus for efficiently treating fluids with light.

It is another object of this invention to provide a method and apparatus for more completely treating fluids with light.

It is another object of this invention to provide a method and apparatus for more speedily treating fluids with ultraviolet light.

It is yet another object of this invention to provide a method of treating a thin layer of fluid with concentrated light.

It is another object of this invention of this invention to provide a method for more effectively treating fluid with ultraviolet light by presenting the fluid in a thin layer to concentrated light.

In accordance with this invention, there is provided apparatus for treating fluids comprising a high intensity light source, fluid passageway means for carrying a stream of fluid through said apparatus in a thin layer, and means for concentrating light from said light source on said fluid layer.

Further in accordance with one embodiment of this invention, an apparatus for treating fluid with light comprises an internally reflective elliptical cylinder, having a first light source focus and a second object focus, an elongated light source at said first focus, and a light-transparent, annular fluid conduit at the other focus.

Further, in accordance with this invention, there is provided a method of irradiating a fluid comprising forming said fluid into a thin film, providing an elongated light source having a power input of at least about 200 watts per inch of light-emitting bulb length, and concentrating the light emitted from said bulb on said thin film of liquid.

Description of the Preferred Embodiments

Figure 1:
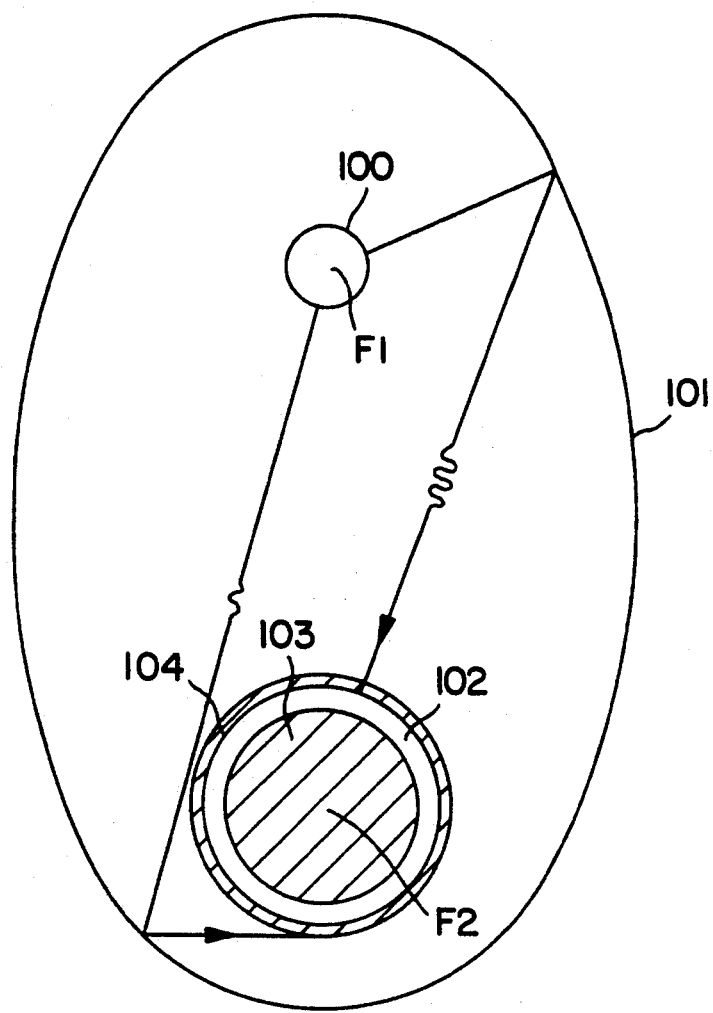
FIG. 1 is a schematic drawing illustrating an embodiment of this invention comprising an elliptical reflector and an annular fluid conduit.

FIG. 1 is a schematic illustration of a preferred embodiment of this invention. A light source 100, preferably a high intensity discharge lamp bulb, is located at a first focus F1 of an elliptical cylinder 101. The high intensity discharge bulb could be a microwave electrodeless lamp bulb or an arc-type discharge bulb and may emit radiation in the range from ultraviolet to infrared, preferably ultraviolet.

An annular conduit 102 defined by shaft 103 provided with a reflective surface, and transparent tube 104, is located in the vicinity of the second focus F2 of the elliptical cylinder 101 Depending on the size of the elliptical cylinder 101 it may be necessary to move the center of the conduit 102 a small distance away from the second focus F2 in order to avoid interference between the tube 104 and cylinder 101. Shaft 103 could be replaced by a tube whose outer surface is one element defining the fluid flow passage. Such a tube may be transparent to at least a portion of light to allow radiation to pass through it.

The shape of the conduit is preferably annular; however, the conduit may be in the shape of a crescent or a ring with varying thickness.

The elliptical cylinder 101 is made of material which is highly reflective of ultraviolet radiation, such as, for example, anodized aluminum.

It is known that light emanating from one focus of an ellipse will be incident on the other focus. Thus light emanating from the light source 100 will converge on the fluid conduit 102 located near the second focus.

It is critical to this invention that the light rays converge on the liquid being irradiated. Convergent light rays, as compared with rays radiated in an isotropic manner are intensified and thus more effective. Apparatus constructed in accordance with FIGS. 1-3 will typically concentrate the light on a strip which has a width which is slightly greater than the diameter of the bulb emitting the light.

Another critical factor is that the fluid must be presented for irradiation in a layer sufficiently thin so that the fluid is not deep with respect to the direction of the incident radiation, and the radiation may penetrate without large attenuation to the deepest layers of the fluid.

If the fluid is to be fully treated after one pass through the treatment apparatus, then the thickness of the fluid layer must be adjusted in light of the absorption coefficient of the fluid and the intensity of the concentrated light so that the full depth of the fluid is effectively treated by the light. The flow rate of fluid is also a factor in determining whether the fluid at full depth receives sufficient radiation. Useful fluid thickness may range from less than about 0.0625 inch to over 0.15 inch.

Preferably the cross-sectional area of the annular conduit will be made small enough so that the flow in the conduit is turbulent. Turbulent flow serves two purposes. First, it mixes the layers of fluid. Though this invention teaches the combination of a thin fluid layer and concentrated light to eliminate preferential irradiation of the outermost liquid, a difference in irradiation through the thickness of the fluid may remain and the mixing resulting from turbulent flow tends to negate the effect of the gradient. Second, if the fluid tends to form a precipitate of light-blocking material on the inside of the tube, the turbulent flow will tend to break up the deposits. The dimensions for a cross-section area which will provide turbulent flow can be determined by approximate formulas based on flow in a pipe that are well-known in fluid mechanics. With a given flow space cross-section, the rate of fluid flow can be increased to obtain turbulent flow. To better accomplish the above two mentioned results of turbulent flow, the fluid flowing will preferably have a Reynolds number above about 80,000.

Figure 2:
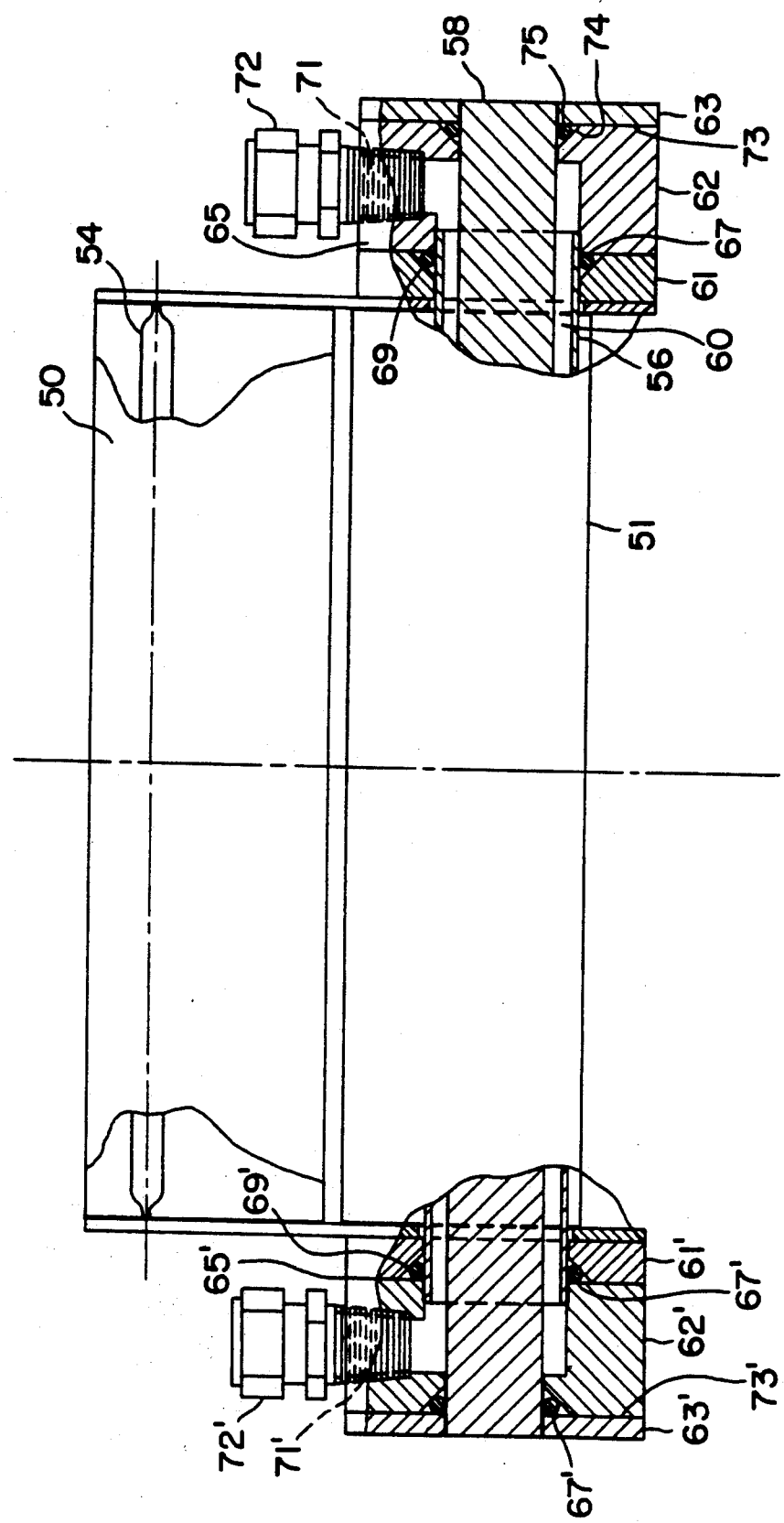
FIG. 2 is a sectional view in elevation of the embodiment of this invention shown in FIG. 1.

FIG. 2 depicts a preferred embodiment of this invention which corresponds to the schematic illustration of FIG. 1. Upper 50 and lower 51 elliptical shells serve as focusing reflectors, and constitute an elliptical cylinder. An elongated light source 54, preferably a discharge bulb, is located parallel to the cylinder at a first focus. The discharge bulb 54 may be an arc lamp in which case suitable electric power connections as known in the art would be provided.

The discharge bulb may be a microwave electrodeless lamp. In this case a screen is extended across the edges of the upper elliptical shell to retain microwaves therein. The complete metal enclosure formed by the screen, the end walls, and the shell functions as a microwave cavity. A microwave coupling iris is provided on the wall of the cavity, and a microwave source is associated with a wave guide. Lamps of this sort are known. As an example U.S. Pat. No. 8,042,850 to Ury et al teaches a lamp which may readily be adapted to be used as the light source for this invention.

A transparent tube 56, which may be vitreous silica or alumina but is preferably silica, and a rod 58, preferably made out of stainless steel, fit within the elliptical shell. Tube 56 and rod 58 define an annular fluid passage 60. The tube could be made out of other materials that have the required transmissivity, chemical resistance, and mechanical properties to sustain the fluid pressure. The rod 58 could also be made from numerous other materials. The materials of the rod 58 and tube 56 are selected for their resistance to actinic radiation-induced chemical activity.

An assembly comprising a set of first 61, second 62, and third 63 metal rings is provided on the ends of the combination of rod 58 and tube 56. The assembly of these rings serves to locate the rod 58 and tube 56 and provides connections to the annular conduit 60 for flowing fluid. Only one assembly will be described since the assemblies for right and left ends are identical. One end can be chosen as the outlet and the other as the inlet. The rod 58, which is longer than the tube 56, extends outside tube 56 at each end. First ring 61 and a first end 65 of second ring 62 have inside diameters that fit the outside of the tube 56. First ring 61 is beveled on the inner circumference on the side facing second ring 62. An 0-ring 67 is squeezed between a bevel 69 of first ring 61 and second ring 62, which is bolted against it. Tube 56 extends past first ring 61 and into second ring 62. 0-ring 67 is squeezed inwardly towards tube 56 and seals it from external leakage. Second ring 62 has a radial threaded hole 71 which connects with a fluid coupling 72. Tube 56 does not extend as far as threaded hole 71 and therefore does not block it. Beyond threaded hole 71 a second side 73 of second ring 62 adjacent third ring 63 is stepped down to a smaller inside diameter, roughly the diameter of metal rod 58. The outwardly facing inner edge of the step 73, on the outside of second metal ring 62 is provided with a bevel 74. Similar to the arrangement hereinabove described third ring 63 which is not beveled and also has an inner diameter approximating that of rod 58 is bolted onto second end 73 of second ring 62. A second 0-ring 75 is squeezed between beveled edge 74 of second ring 62 and third ring 63. Rod 58 extends beyond the abutting faces of second ring 62 and third ring 63. 0-ring 75 forms a fluid seal between second ring 62 and rod 58. As seen in the drawing and described above, similar sealing and fluid coupling means are used on each end of the rod tube arrangement elements on the left end being identified by prime numerals.

Fluid which is to be irradiated is introduced through fluid coupling 72 and passes into annular flow space 60 between tube 56 and rod 58, and exits on the other side in a like manner. A reliable sealing means is thus provided for transferring fluid from a standard round fluid conduit to the special annular fluid conduit of this invention.

Figure 3:
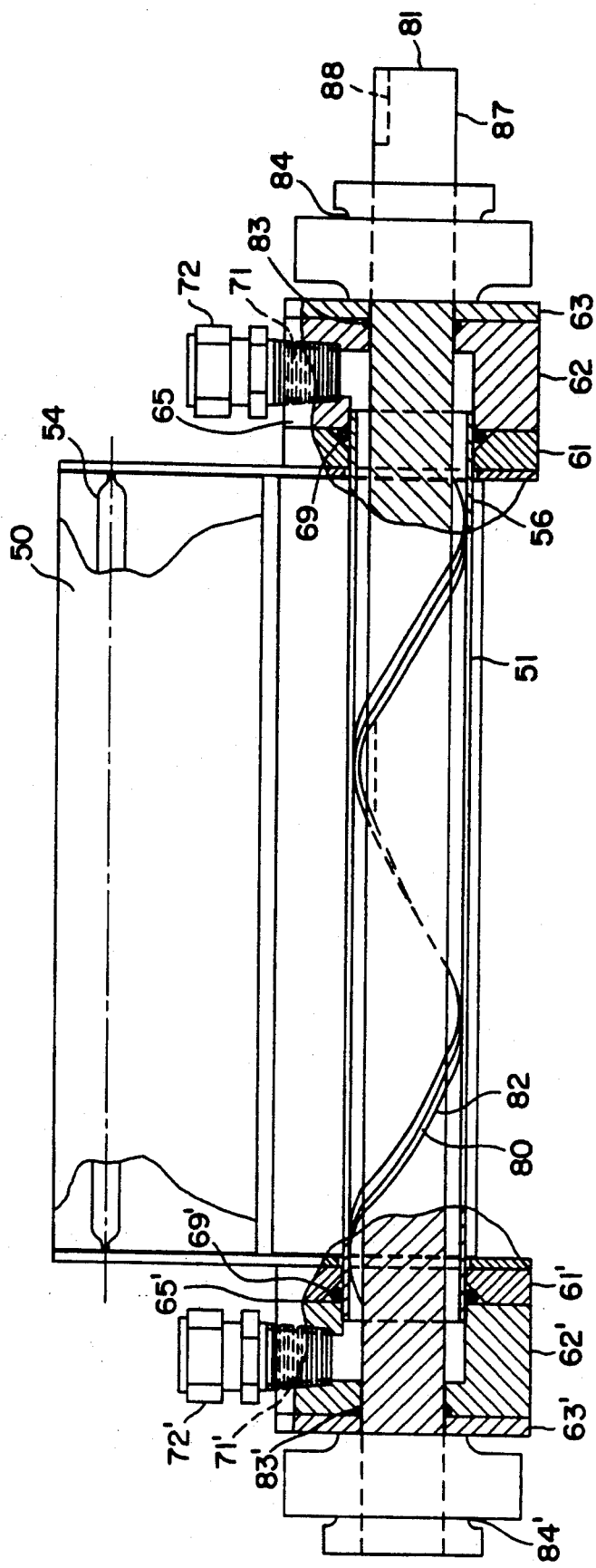
FIG. 3 shows a modification of the embodiment of the invention shown in FIG. 2.

The light source used in this invention is preferably a high power ultraviolet light source. The source used in the preferred embodiment described above is elongated (linear). A high power linear lamp, as referred to in this specification, is a lamp with an input power of at least about 200 watts per inch (W/in) of lamp length, and preferably with an input power in the range of about 350 to about 650 watts per inch of bulb length. If the turbulent flow is not sufficient to keep the inside of the tube clear of deposits, a wiper mechanism, such as is shown in FIG. 3, may be incorporated into the device. In FIGS. 2 and 3, the same numerals refer to the same parts. Referring to FIG. 3, a rubber wiper blade 80 is held in a groove 82 in a rod 81. As depicted, groove 82 and wiper blade 80 preferably form a helix around rod 81. The helical shape has the advantage that it provides axial movement of the debris towards one end. However, for manufacturing simplicity the wiper and groove could be straight. Bevel 74 in the stepped down second side of the second plate, as shown in FIG. 2, is replaced with a small step 83 to a slightly larger diameter at the edge of the second plate. Support bearings 84 are attached to the outside of the third plate 63. A shaft 81 extends through bearings 84 on either side of the apparatus. On at least one end 87 shaft 81 is extended beyond bearings 84. Extended end 87 of shaft 81 has a key groove 88 so that it can be attached to a rotation means such as a pulley or hand crank.

Thus, means are provided for rotating the shaft 81 relative to the apparatus including tube 56. Wiper blade 80 which is fixed to the shaft 81 wipes the inside of tube 56 when shaft 81 is rotated. For the embodiment in which wiper 80 is helical, shaft 56 should be rotated so that the wiper 80 urges the material to move in the same direction that the fluid flows.

Figure 4:
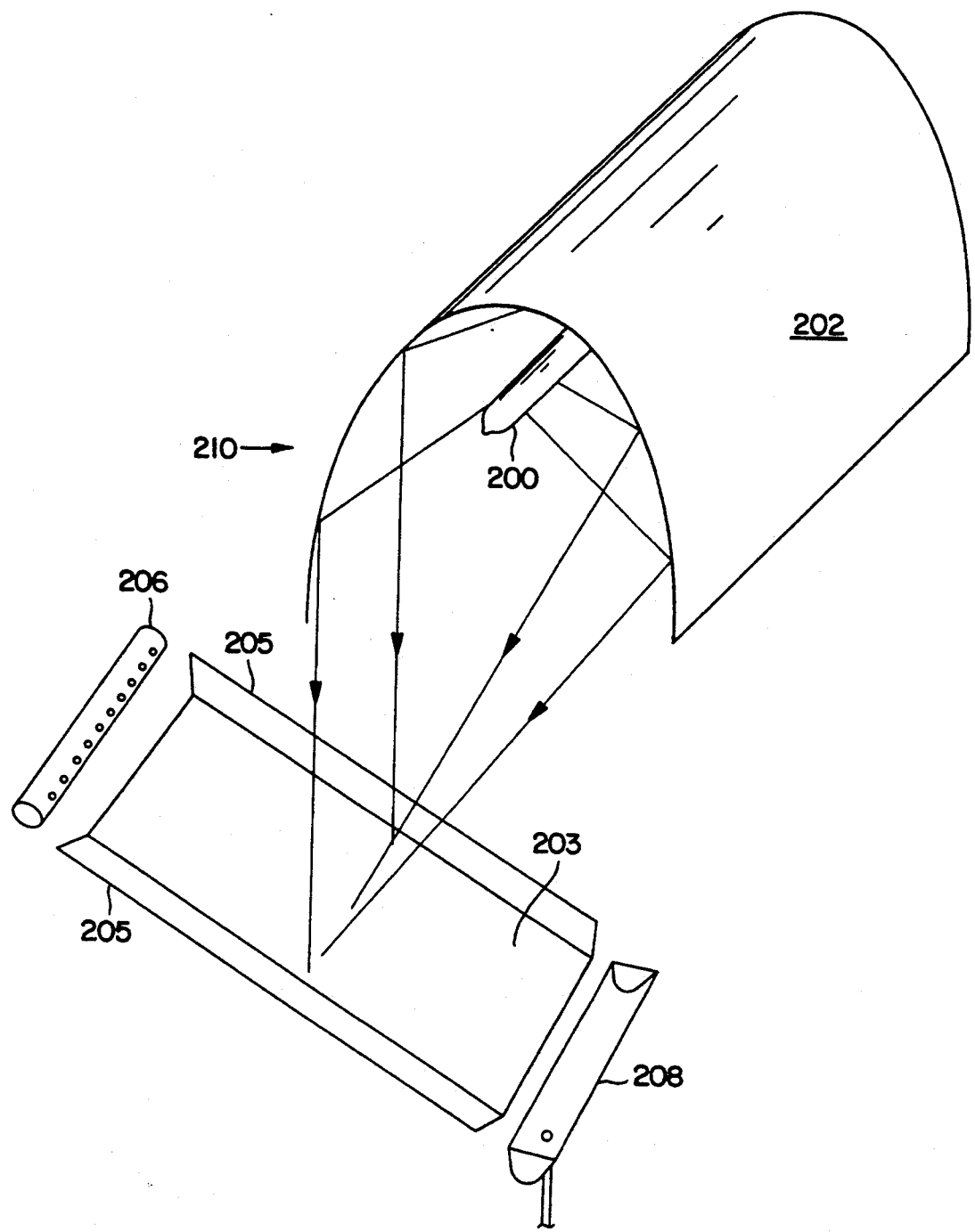
FIG. 4 shows an embodiment in which a light source which focuses irradiation on a narrow strip is used to irradiate a fluid flowing over that surface in a thin layer.

FIG. 4 shows another embodiment of the present invention. In this embodiment of the invention, a lamp 210 comprises an elliptical reflector 202 and an elongated discharge bulb, or linear bulb, 200, positioned at a first focus of reflector 202. Reflector 202 focuses light from bulb 200 on a narrow strip at the position of the second geometric focus of the elliptical cylinder. Such an optical design is known. A tray 203 which has side edges 205 bent upwardly to prevent spillage is used to carry fluid through the irradiation zone of lamp 210. Tray 203 is inclined and located so that the second focal line of lamp 210 falls across its surface. Fluid which is sprayed onto the tray 203 by a sparger 206 tends to distribute in a thin layer as it flows down tray 203. The fluid flowing off the opposite end of the tray is collected in a trough 208. Both sparger 206 and trough 208 are connected to fluid circulation and storage means which are not shown.

Figure 5:
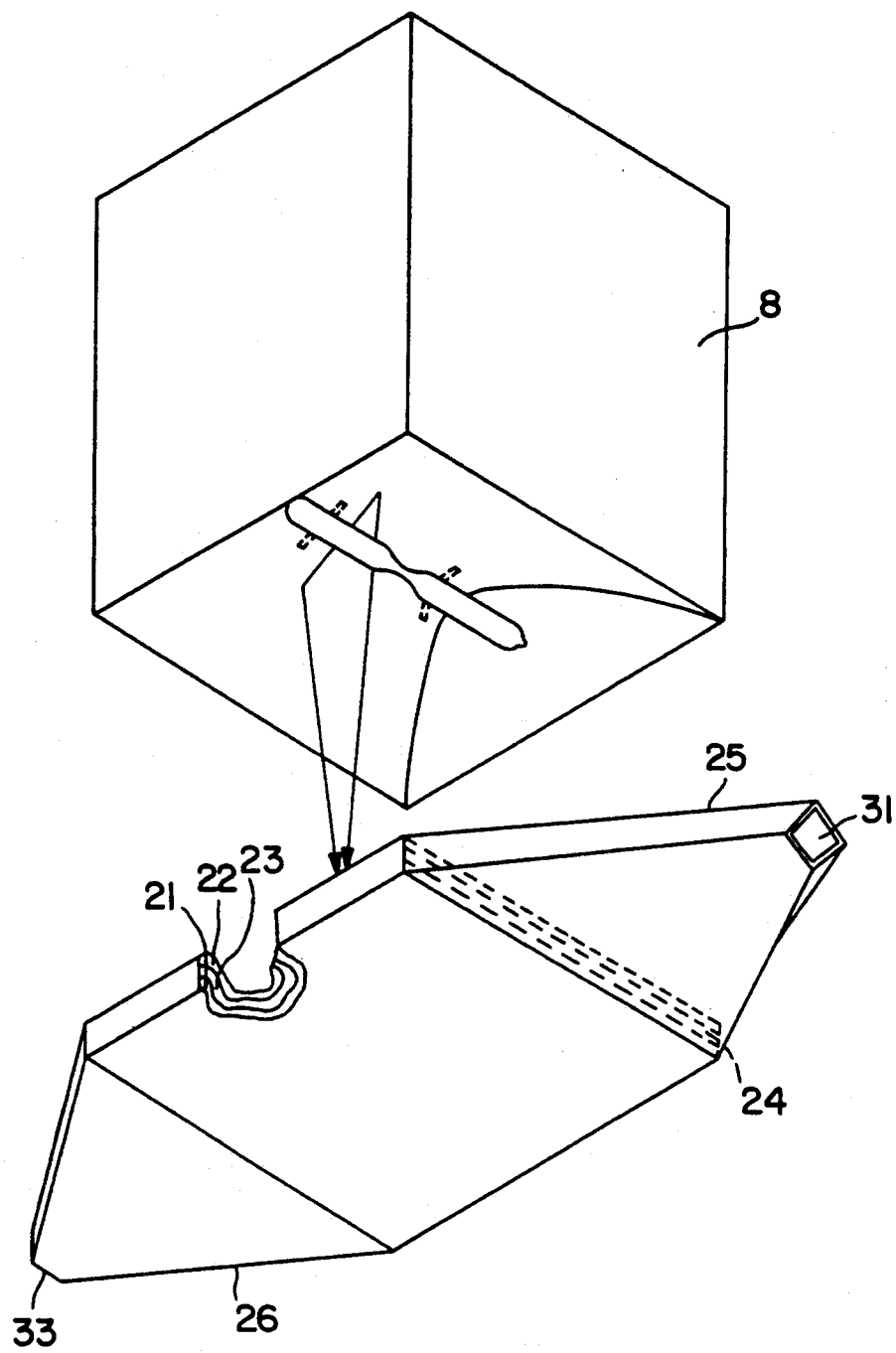
FIG. 5 shows an embodiment in which a light source which focuses its radiation on a narrow strip is used to irradiate fluid flowing in a flat conduit.

FIG. 5 shows yet another embodiment of the present invention. In this embodiment, a light source 8 is a high intensity ultraviolet light source. The optical arrangement is the same as described in connection with and shown in FIG. 4. The fluid conduit is comprised of a bottom plate 21 and a transparent plate 22 which define a shallow flow zone 23. One end 24 of the conduit is coupled to an inlet funnel 25 and the opposite end is coupled to an outlet funnel 26. Light source 8 is positioned so that its focused rays fall on a line across, i.e., perpendicular to the flow of fluid in the fluid flow zone 23. The flow between the plates should preferably be turbulent if the fluid being treated tends to precipitate materials.

Having thus described the present invention, the following Example is offered to illustrate it in detail.

EXAMPLE

Apparatus constructed in accordance with FIGS. 1 and 2 for irradiating a fluid comprises a 45° elliptical reflector having a major axis 6" long.

An elongated light source 10 inches long and 0.8 inch in diameter is positioned at one focus of the reflector and an annular passage is positioned at the other focus. The annular passageway is defined by an 1.2 inch O.D. inner shaft coaxially aligned with a transparent tube having a 1.5 inch I.D. to form a 0.15 inch thick flow path. The bulb is energized at an input power of about 375 watts per inch of bulb length.

The arrangements described herein are intended to be exemplary only and are not intended to limit the scope of the invention, which should be limited only by the claims which follow.

What is claimed:

1. Apparatus for treating a fluid with light comprising:
   a high intensity light source, wherein said light source is an elongated discharge bulb;
   fluid flow passage means for conducting a stream of fluid through said apparatus in a layer sufficiently thin so that the full depth of the fluid is treated by light from said light source, said passage means comprising an outer, light-transparent tubular member and an inner member coaxial with and spaced from said outer member to form an annulus for flowing said fluid therethrough, said inner member being provided with a reflective outer surface; and,
   means for reflecting light from said light source and concentrating the reflected light on said fluid layer, said means for reflecting and concentrating light comprising at least one reflector in the configuration of a substantially complete, elliptical cylinder having a first focus and a second focus, said discharge bulb being positioned coaxially with said first focus and at least a portion of said fluid conduit being positioned at said second focus.

2. Apparatus according to claim 1 wherein said discharge bulb is a microwave electroless discharge bulb.

3. Apparatus according to claim 1 wherein said discharge bulb is an arc lamp.

4. Apparatus according to any one of claims 1, 2, or 3 wherein said discharge bulb is provided with means for providing an input power of at least about 200 watts per inch of light-emitting bulb length.

5. Apparatus according to any one of claims 1, 2, or 3 wherein said discharge bulb is provided with means for providing an input power from about 350 to about 650 watts per inch of light-emitting bulb length.

* * * * *